(12) United States Patent
Orbay et al.

(10) Patent No.: US 8,394,098 B2
(45) Date of Patent: *Mar. 12, 2013

(54) MODULAR FRACTURE FIXATION PLATE SYSTEM

(75) Inventors: Jorge L. Orbay, Miami, FL (US); Javier E. Castaneda, Miami, FL (US); Edward Mebarak, Miami Beach, FL (US); Jose Luis Francese, Miami Springs, FL (US); Robert Sixto, Jr., Miami, FL (US)

(73) Assignee: Biomet C. V., Gibraltar (GI)

( * ) Notice: Subject to any disclaimer, the term of this patent is extended or adjusted under 35 U.S.C. 154(b) by 1840 days.

This patent is subject to a terminal disclaimer.

(21) Appl. No.: 11/378,703

(22) Filed: Mar. 17, 2006

(65) Prior Publication Data

US 2006/0235404 A1 Oct. 19, 2006

Related U.S. Application Data

(63) Continuation-in-part of application No. 11/082,401, filed on Mar. 17, 2005.

(51) Int. Cl.
*A61B 17/80* (2006.01)

(52) U.S. Cl. .......................................................... 606/71

(58) Field of Classification Search .................. 606/60, 606/280, 70, 71, 281, 286, 289, 291, 295, 606/301; 403/292, 311, 312; 411/378, 393
See application file for complete search history.

(56) References Cited

U.S. PATENT DOCUMENTS

| | | | |
|---|---|---|---|
| 1,105,105 A | 7/1914 | Sherman | |
| 2,406,832 A | 9/1946 | Hardinge | |
| 2,486,303 A | 10/1949 | Longfellow | |
| 3,488,779 A | 1/1970 | Christensen | |
| 3,695,259 A | 10/1972 | Yost | |
| 4,219,015 A | 8/1980 | Steinemann | |
| 4,506,662 A | 3/1985 | Anapliotis | |
| 4,683,878 A | 8/1987 | Carter | |
| 4,776,330 A | 10/1988 | Chapman et al. | |
| 4,781,183 A | 11/1988 | Casey et al. | |
| 4,867,144 A | 9/1989 | Karas et al. | |
| 4,955,886 A | 9/1990 | Pawluk | |
| 4,957,497 A | 9/1990 | Hoogland et al. | |
| 5,002,544 A | 3/1991 | Klaue et al. | |
| 5,015,248 A | 5/1991 | Burstein et al. | |
| 5,041,114 A | 8/1991 | Chapman et al. | |
| 5,053,036 A | 10/1991 | Perren et al. | |
| 5,127,914 A * | 7/1992 | Calderale et al. | 606/65 |
| 5,129,899 A | 7/1992 | Small et al. | |
| 5,190,544 A | 3/1993 | Chapman et al. | |
| 5,209,751 A | 5/1993 | Farris et al. | |

(Continued)

FOREIGN PATENT DOCUMENTS

| | | |
|---|---|---|
| EP | 0471419 A2 | 2/1992 |
| EP | 0773004 A1 | 5/1997 |

(Continued)

*Primary Examiner* — Eduardo C Robert
*Assistant Examiner* — David Comstock
(74) *Attorney, Agent, or Firm* — Gordon & Jacobson, PC

(57) ABSTRACT

A fracture fixation plate system for use on a long bone having a metaphysis and a diaphysis, includes at least one end plate having a head portion for the metaphysis, and at least one fragment plate having a first end and a second end with a plurality of screw holes therebetween. The end plate includes mating structure adapted to mate with and securely couple to at least one end of the at least one fragment plate. The system preferably includes several end plates and fragment plates to accommodate anatomy of various sizes.

11 Claims, 12 Drawing Sheets

U.S. PATENT DOCUMENTS

| | | | |
|---|---|---|---|
| 5,364,398 A | | 11/1994 | Chapman et al. |
| 5,364,399 A | * | 11/1994 | Lowery et al. ............... 606/295 |
| 5,474,553 A | | 12/1995 | Baumgart |
| 5,484,439 A | * | 1/1996 | Olson et al. .................... 606/65 |
| 5,578,036 A | | 11/1996 | Stone et al. |
| 5,601,553 A | | 2/1997 | Trebing et al. |
| 5,616,142 A | | 4/1997 | Yuan et al. |
| 5,620,445 A | | 4/1997 | Brosnahan et al. |
| 5,733,287 A | | 3/1998 | Tepic et al. |
| 5,772,662 A | | 6/1998 | Chapman et al. |
| 5,827,286 A | * | 10/1998 | Incavo et al. .................... 606/71 |
| 5,906,644 A | | 5/1999 | Powell |
| 5,975,904 A | | 11/1999 | Spiegel |
| 6,001,099 A | | 12/1999 | Huebner |
| 6,340,362 B1 | | 1/2002 | Pierer et al. |
| 6,383,186 B1 | | 5/2002 | Michelson |
| 6,645,208 B2 | | 11/2003 | Apfelbaum et al. |
| 6,669,700 B1 | | 12/2003 | Farris et al. |
| 6,699,249 B2 | | 3/2004 | Schlapfer et al. |
| 7,604,657 B2 | | 10/2009 | Orbay et al. |
| 7,635,381 B2 | | 12/2009 | Orbay |
| 8,128,628 B2 | | 3/2012 | Freid et al. |
| 2002/0013586 A1 | * | 1/2002 | Justis et al. ..................... 606/61 |
| 2003/0060828 A1 | | 3/2003 | Michelson |
| 2004/0087953 A1 | | 5/2004 | Singhatat et al. |
| 2004/0102778 A1 | | 5/2004 | Huebner et al. |
| 2004/0167521 A1 | * | 8/2004 | De Windt ........................ 606/69 |
| 2004/0193155 A1 | | 9/2004 | Castaneda |
| 2004/0210221 A1 | * | 10/2004 | Kozak et al. ................... 606/69 |
| 2004/0260291 A1 | * | 12/2004 | Jensen ............................ 606/69 |
| 2005/0049594 A1 | | 3/2005 | Wack et al. |
| 2005/0154392 A1 | | 7/2005 | Medoff et al. |
| 2005/0187551 A1 | | 8/2005 | Orbay et al. |
| 2005/0240187 A1 | | 10/2005 | Huebner et al. |
| 2006/0100625 A1 | | 5/2006 | Ralph et al. |
| 2006/0229619 A1 | | 10/2006 | Orbay et al. |
| 2006/0235404 A1 | | 10/2006 | Orbay et al. |
| 2007/0260244 A1 | | 11/2007 | Wolter |

FOREIGN PATENT DOCUMENTS

| | | |
|---|---|---|
| FR | 2367479 A1 | 5/1978 |
| GB | 2072514 A | 10/1981 |
| JP | 11299804 | 2/1999 |
| JP | 11128245 | 5/1999 |
| JP | 11-290359 | 10/1999 |
| JP | 2003052709 | 2/2003 |
| WO | WO99/44529 | 9/1999 |
| WO | WO2004045389 A2 | 6/2004 |
| WO | WO2006/102081 A1 | 9/2006 |

* cited by examiner

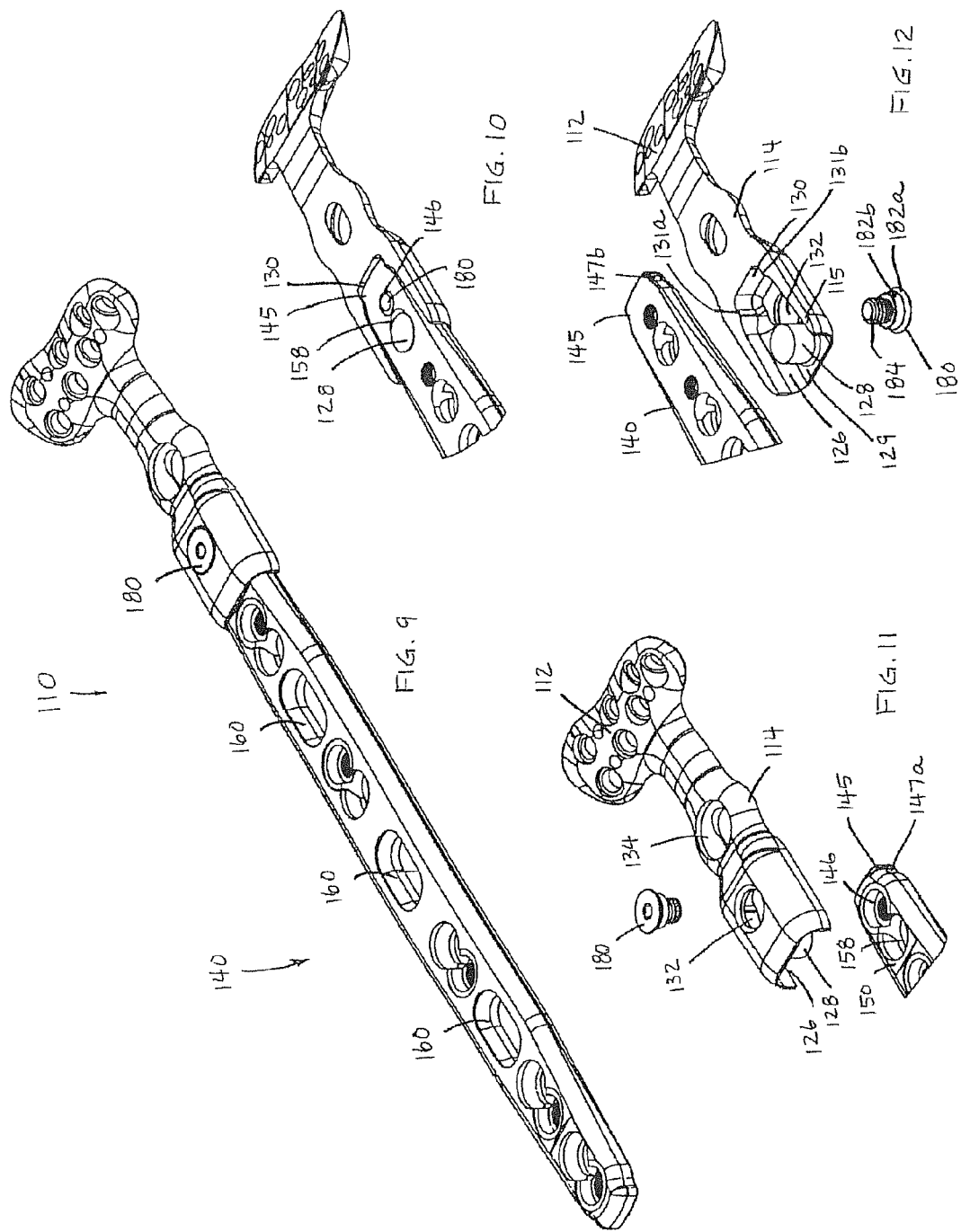

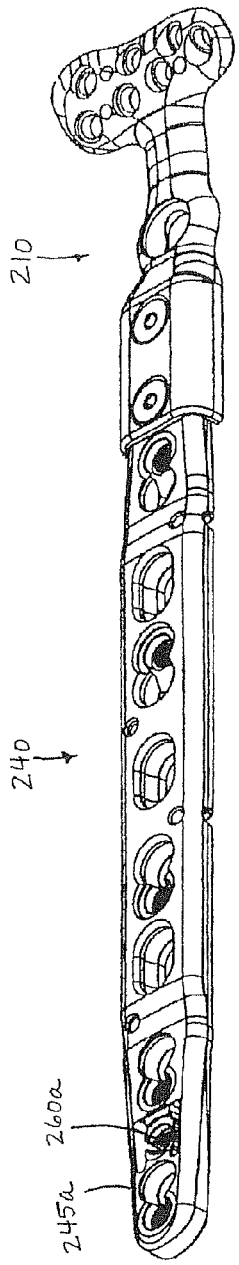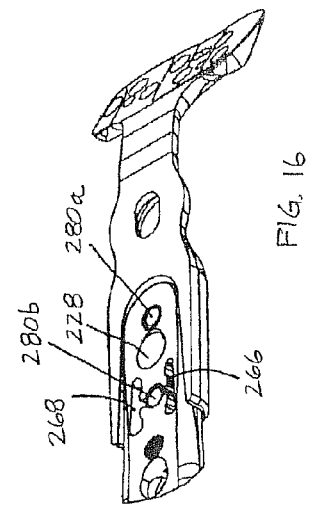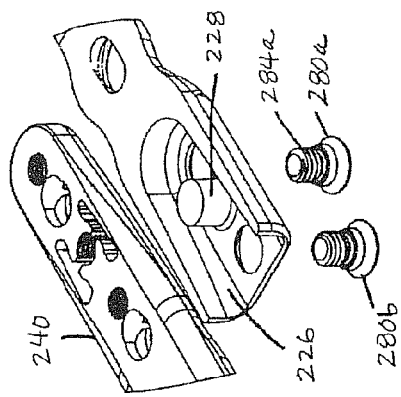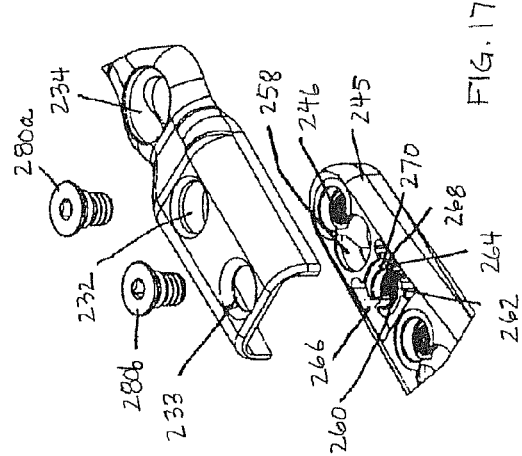

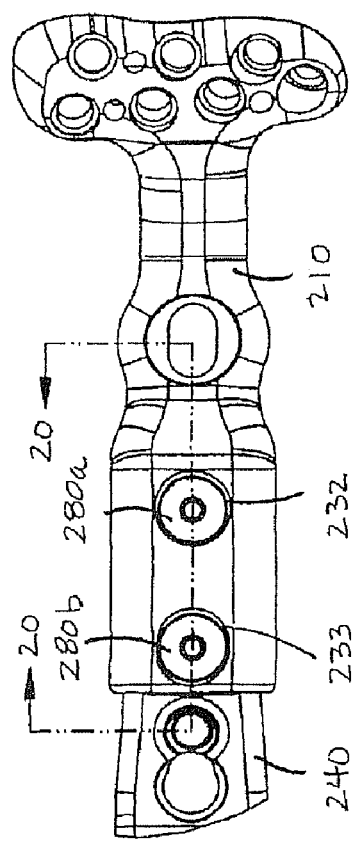
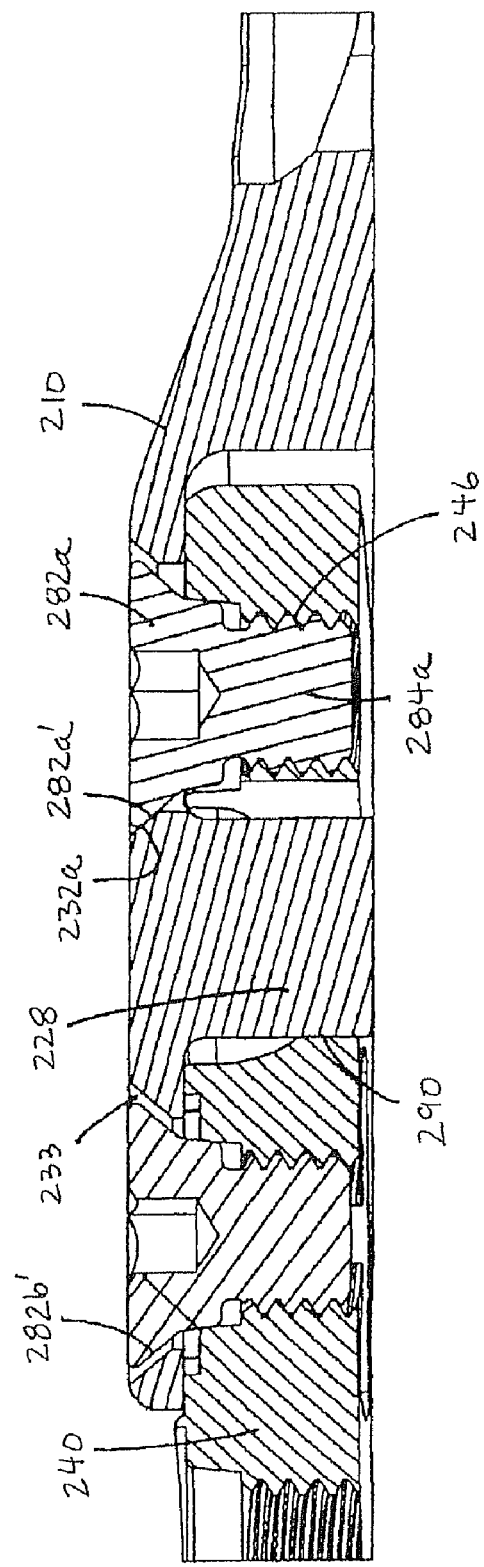
FIG. 19
FIG. 20

MODULAR FRACTURE FIXATION PLATE SYSTEM

CROSS-REFERENCE TO RELATED APPLICATIONS

This application is a continuation-in-part of U.S. Ser. No. 11/082,401, filed Mar. 17, 2005, issued on Nov. 22, 2011, as U.S. Pat. No. 8,062,296, which is hereby incorporated by reference herein in its entirety.

This application is also related to U.S. Ser. No. 10/985,598, filed Nov. 10, 2004, issued on Dec. 22, 2009, as U.S. Pat. No. 7,635,381, and U.S. Ser. No. 11/040,779, filed Jan. 21, 2005, now abandoned, which are hereby incorporated by reference herein in their entireties.

BACKGROUND OF THE INVENTION

1. Field of the Invention

This invention relates broadly to surgical implants. More particularly, this invention relates to a bone fracture fixation system.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the dorsal side of a bone, and screws extending from the plate into holes drilled in the bone fragments to provide stabilized fixation of the fragments.

In some cases, a relatively proximal diaphyseal portion as well as the distal metaphyseal portion of the radius may be fractured. In these cases, fragment plates are often used in conjunction with the distal radius plate. There is a disadvantage, however, in using two plates rather than one. It results in unsupported bone between the two implants. The resultant load supported by the bone between the plates in a concentrated manner. Thus, it would be desirable to provide an integrated implant that shares the load across the entire implant for distal and mid-shaft fractures.

U.S. Pat. No. 5,190,544 to Chapman et al. describes a modular plating system including a metaphyseal plate and a diaphyseal plate that are interconnected via a dovetail slot and then secured to the bone with cortical bone screws to lock the plates together. The integrity of such a system is subject to loosening in the event the bone screws loosen their engagement with the bone, e.g., through micromotion. Furthermore, if the bone is of poor quality, e.g., as a result of multiple fractures along the bone portion underlying the components, integrity between the components may never be accomplished. In addition, the metaphyseal component which receives an end of the diaphyseal fragment plate is significantly thicker (approximately 75% percent thicker) and wider (approximately 35% wider) than the fragment plate, providing an undesirably thick metaphyseal plate and creating a potentially irritating transition in two dimensions from the metaphyseal plate to the diaphyseal plate where the metaphyseal plate ends.

SUMMARY OF THE INVENTION

It is therefore an object of the invention to provide a modular fixation system.

It is another object of the invention to provide a modular fixation system that desirably aligns and stabilizes multiple bone fragments in a fracture to permit proper healing.

It is also an object of the invention to provide a modular fixation system that does not rely on the bone for locking the modular components together.

It is a further object of the invention to provide a modular fixation system in which the components are coupled together in a very stable manner to effect a rigid assembly.

It is yet another object of the invention to provide a modular fixation system that, in view of manufacturing variations, will eliminate play between coupled components to increase the load transfer between the coupled components.

It is a yet a further object of the invention to provide a modular fixation system that will not irritate the tissue.

It is an additional object of the invention to provide an improved fixation system that accommodates the anatomical structure of the metaphysis and diaphysis of the radius.

In accord with these and other objects, which will be discussed in detail below, a fracture fixation plate system for the radius according to the invention includes a plurality of different sized distal radius plates (e.g., volar plates or dorsal plates) and a plurality of different sized fragment plates. The distal radius plates are generally T-shaped having a head and a stem substantially transverse thereto. The end of the stem is provided with a mating structure whereby an end of a fragment plate can be coupled to the distal radius plate. The surgeon can select an appropriate size distal radius plate and an appropriate size fragment plate and secure them together prior to implant to form a unified distal radius and fragment plate customized for the patient. This overcomes the disadvantage of using separate distal radius and fragment plates and allows for a wide variety of different sizes while using the minimum number of components. It is an important aspect of the invention that the distal radius plate and fragment plate be joined without reliance on the bone to join them. Otherwise, the tight interface and coupling between the plates could be compromised based on the quality of the bone, which may be fractured beneath the location of the coupling or which may be osteoporotic. In order to secure the distal radius plate and fragment plate together independent of the bone, set screw holes are provided at both ends of the fragment plates. In addition, suitable mating structure is provided at the end of the radius plate stem. The two plates are mated by inserting an end of the fragment plate into a socket at the end of the distal radius plate stem, then inserting one or more set screws through the orthogonal set screw hole to engage threaded set screw hole(s) in the end of the fragment plate. In certain embodiments, means are provided to eliminate any play between the plates.

Additional objects and advantages of the invention will become apparent to those skilled in the art upon reference to the detailed description taken in conjunction with the provided figures.

BRIEF DESCRIPTION OF THE DRAWINGS

FIG. 9 is a perspective view of a second embodiment of a modular plate system according to the invention;

FIG. 10 is a broken bottom perspective view of the embodiment of FIG. 9;

FIG. 11 is a broken top perspective exploded view of the embodiment of FIG. 9;

FIG. 12 is a broken bottom perspective exploded view of the embodiment of FIG. 9;

FIG. 15 is a perspective view of a third embodiment of a modular plate system according to the invention;

FIG. 16 is a broken bottom perspective view of the embodiment of FIG. 15;

FIG. 17 is a broken top perspective exploded view of the embodiment of FIG. 15;

FIG. 18 is a broken bottom perspective exploded view of the embodiment of FIG. 15;

FIG. 19 is a broken top view of the embodiment of FIG. 15; and

FIG. 20 is a section view across line 20-20 in FIG. 19.

DETAILED DESCRIPTION OF THE PREFERRED EMBODIMENTS

Figure 1:
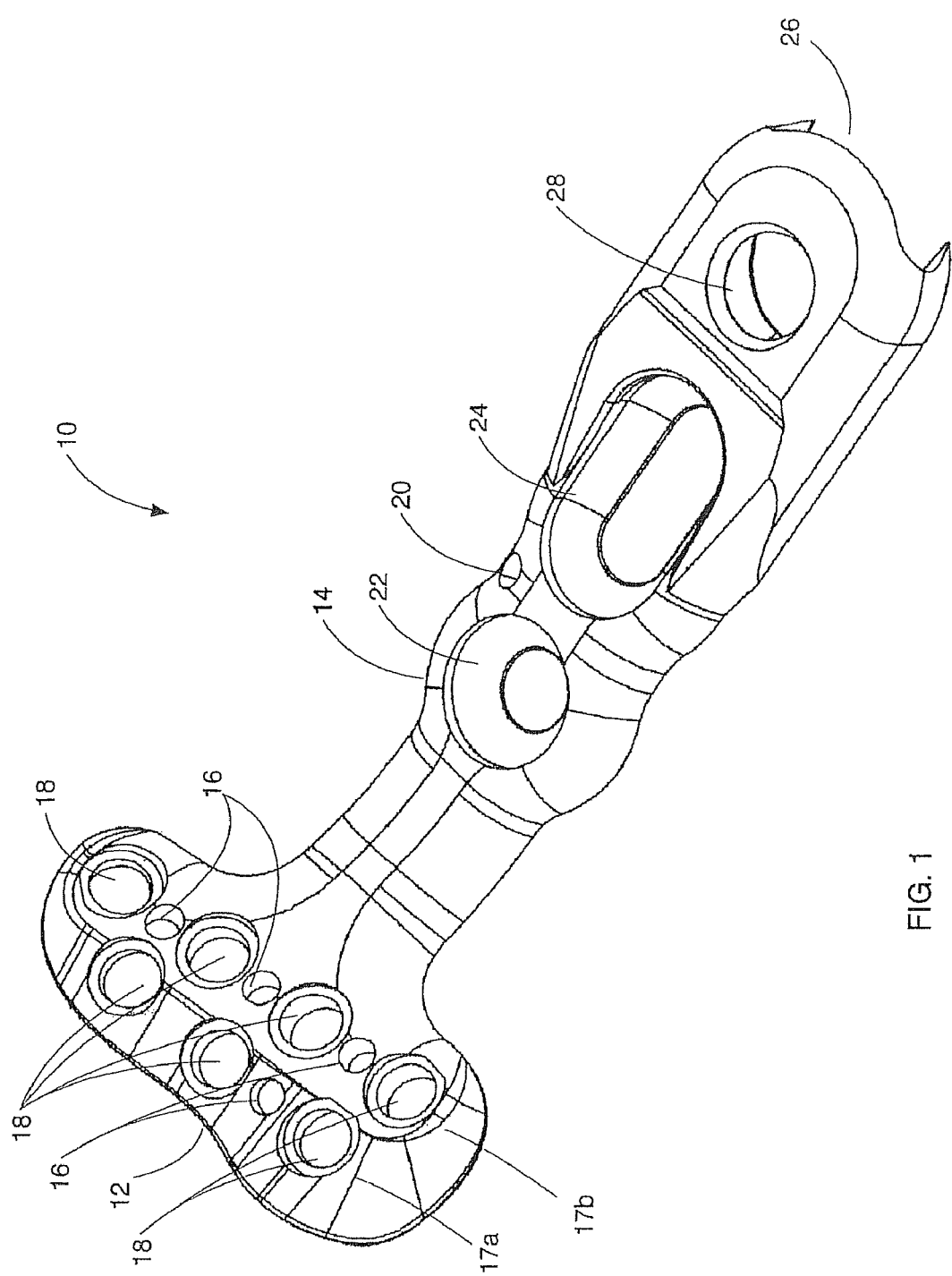
FIG. 1 is a top perspective view of a distal radius volar plate according to the invention.
Figure 2:
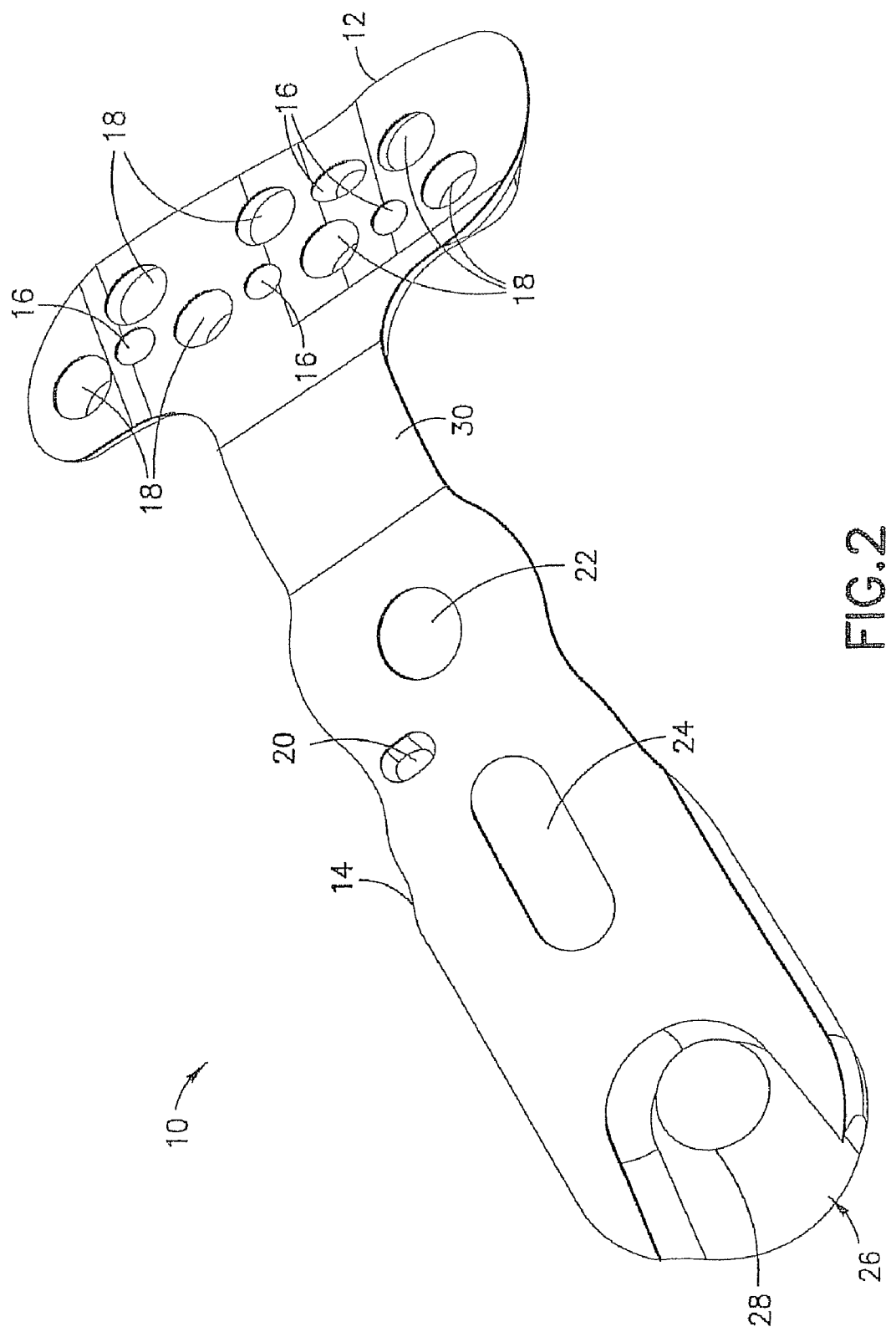
FIG. 2 is a bottom perspective view of the volar plate.

Turning now to FIGS. 1 and 2, a distal radius volar fixation plate (or generally any 'end' plate or metaphyseal plate) 10 includes a distal head portion 12 and a proximal stem portion 14. In a preferred embodiment, the plate 10 corresponds to the plate described in previously incorporated U.S. Ser. No. 10/985,598. However, other metaphyseal plates for different locations on the radius bone or even for placement on different bones or can be used.

The head portion 12 of the volar fixation plate 10 shown has a plurality of alignment holes 16 which are dimensioned to closely accept K-wires in a fixed angle relationship and two longitudinally offset rows 17a, 17b of screw holes 18 for receiving fixation elements therethrough. In a preferred embodiment, the screw holes 18 are threaded, and as such are specifically adapted to receive locking screws and/or pegs that lock in axial alignment relative to the plate.

The stem portion 14 has at least one alignment hole 20 dimensioned to closely accept a K-wire and may optionally include one or more (two as illustrated) bone screw holes 22, 24. That is, the stem may be substantially shorter than shown and does not need to include a bone screw hole. The free end of the stem portion 14 includes a socket in the form of a slot 26 (for receiving an end of the fragment plate 40, described below) and an orthogonal set screw hole 28 intersecting the slot. As shown in FIGS. 1-8, the slot 26 is open to the proximal end of the stem portion, and preferably is also open on the bottom side of the stem portion as well.

From FIGS. 1-8, it will be appreciated that the top side (FIG. 1) of the volar plate 10 has a topography of curved surfaces and recesses surrounding some of the holes to provide a low profile when seated on the anatomical bone surface. The bottom side (FIG. 2) of the head portion 12 is likewise constructed to conform to the anatomy, while the stem portion 14, however presents a smooth surface. The bottom of the head portion 12 lies in a first plane and the stem portion 14 lies in a second plane. A neck 30 transitions between the two planes. The angle between the two planes is preferably approximately 25 degrees.

The alignment holes and the bone screw holes are used as described in previously incorporated U.S. Ser. No. 10/985, 598. The slot 26 and the set screw hole 28 are used in conjunction with a fragment plate and a set screw as described in more detail below.

Figure 3:
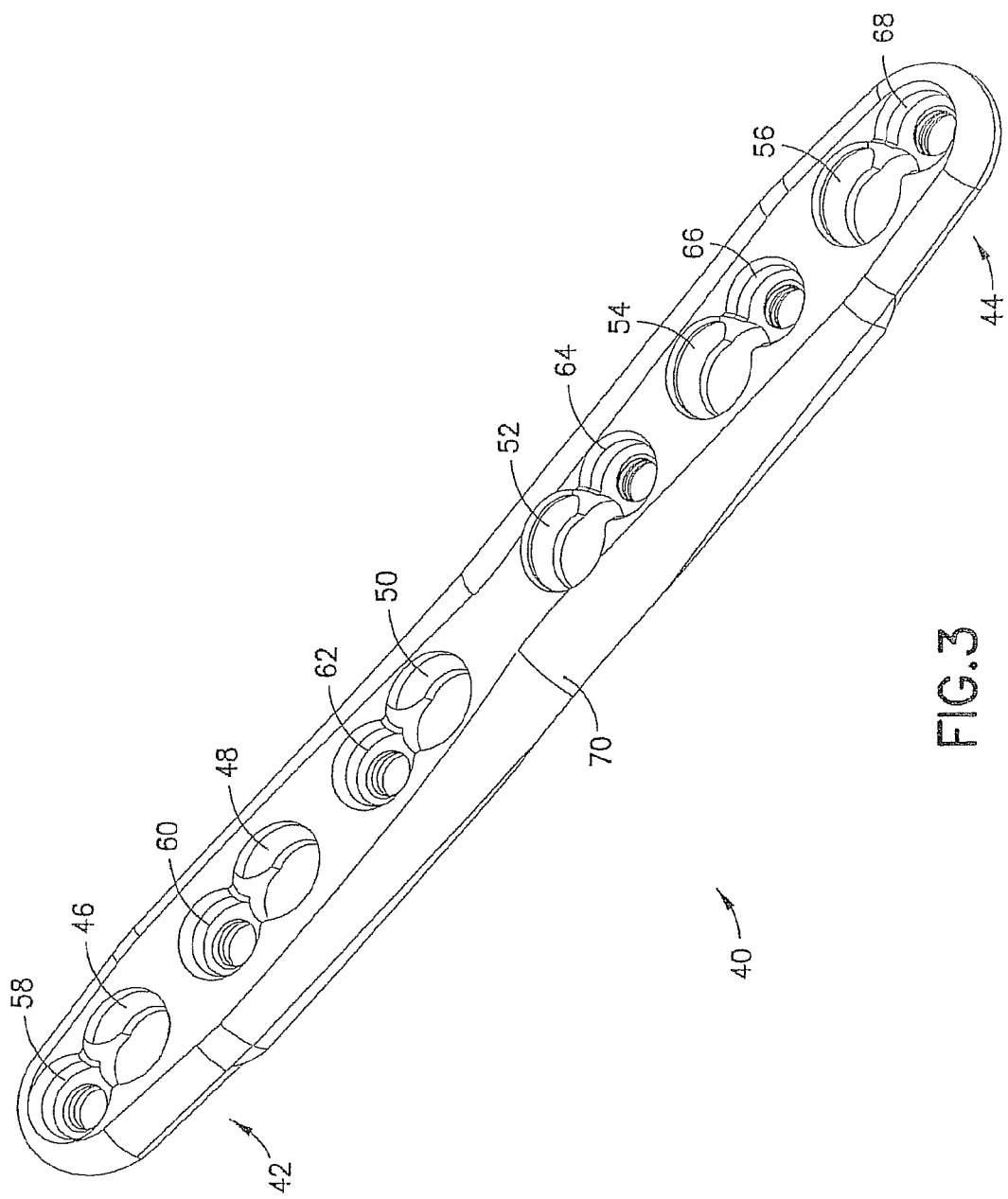
FIG. 3 is top perspective view of a fragment plate according to the invention.
Figure 4:
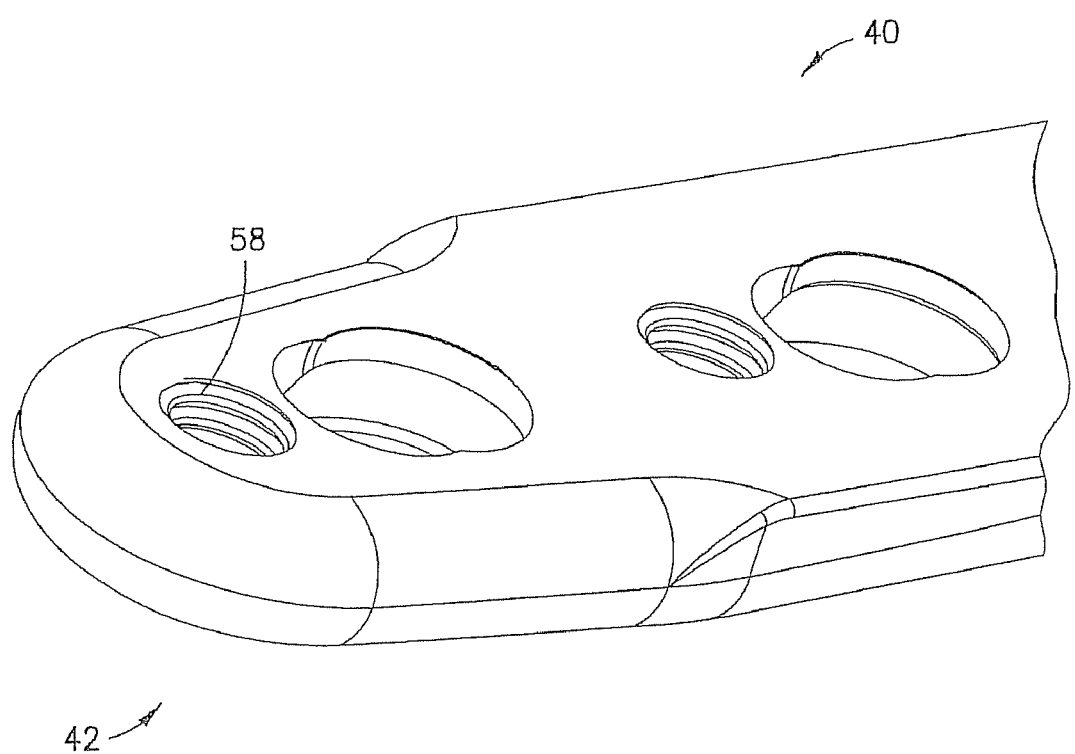
FIG. 4 is an enlarged broken bottom perspective view of an end of the fragment plate.
Figure 5:
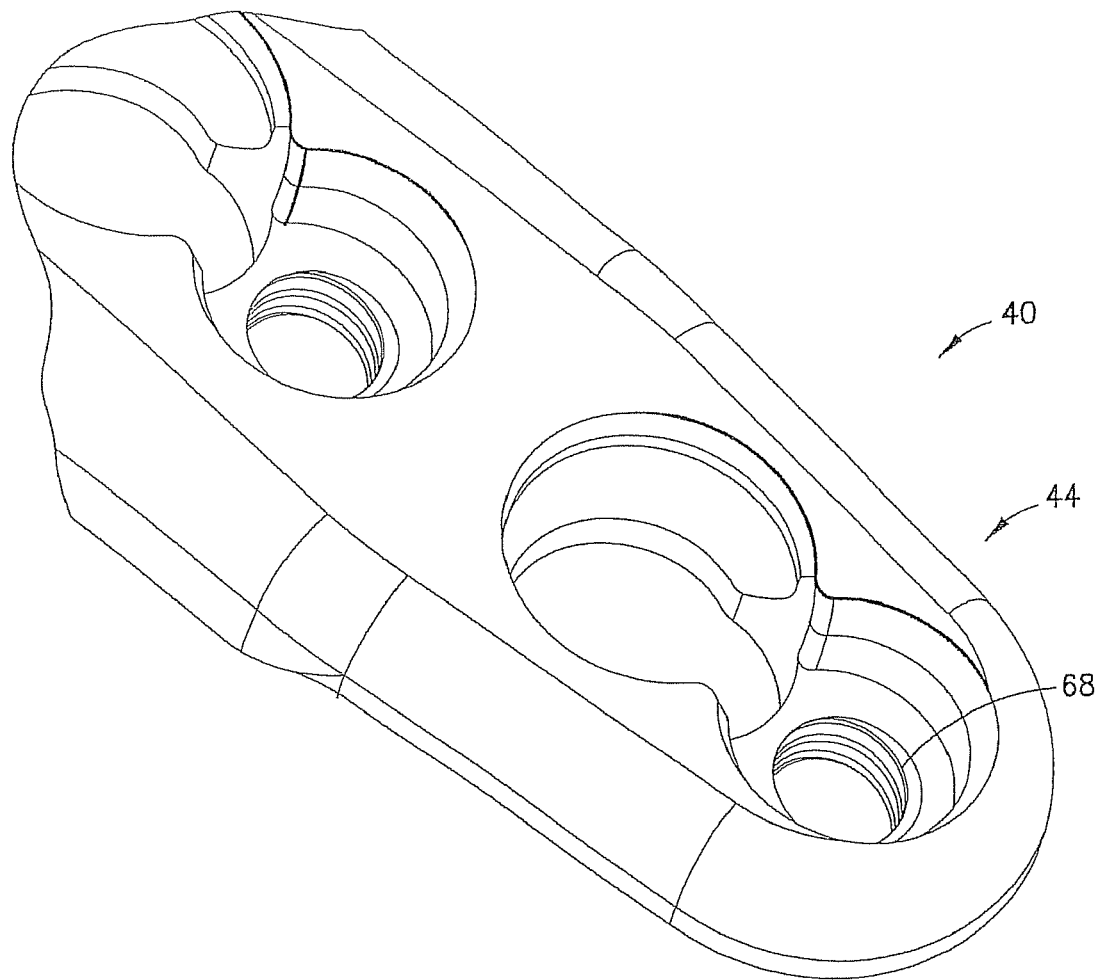
FIG. 5 is an enlarged broken top perspective view of an end of the fragment plate.

Turning now to FIGS. 3-5, an exemplary fragment plate (or diaphyseal plate) 40 according to the invention is illustrated. The fragment plate 40 is an elongate plate having a first end 42 and a second end 44. A plurality of bone screw holes 46, 48, 50, 52, 54, 56 are spaced along the length of the plate for receiving bone screws, and a threaded set screw hole 58, 60, 62, 64, 66, 68 is arranged adjacent each bone screw hole. More particularly, such screw holes are preferably any of the screw holes and associated locking systems described in U.S. Pub. No. 20050187551 A1, incorporated by reference herein, for the reasons and advantages provided therein, although any suitable bone screw hole may be used.

As illustrated, the shape of the fragment plate 40 and the arrangement of holes are preferably longitudinally symmetrical about a mid point 70. Each set screw hole is provided on a side of a bone screw hole closer to an end of the fragment plate than the midpoint of the plate, with a set screw hole 58, 68 specifically being located at each end of the plate. As seen best in FIGS. 4 and 5, the ends 42, 44 of the plate are tapered as well as rounded. The taper occurs over a significant length which permits both a bone screw hole 46, 56 and a set screw hole 58, 68 to be located in the tapered ends 42, 44 of each plate. Comparing FIGS. 4 and 5 with FIGS. 1 and 2, it will be appreciated that the ends 42, 44 of the plate 40 are shaped and dimensioned to fit neatly into the slot 26 of the volar plate 10 with the set screw hole 58, 68 of the plate 40 aligning with the set screw hole 28 of the plate 10. This is illustrated more clearly in FIG. 6. The taper at the end of the fragment plate 40 permits the remainder of the fragment plate and the stem 14 of the end plate 10 to have substantially the same width, e.g., approximately 0.43" for a distal radius fixation system. It is noted that both ends 42, 44 of the fragment plate preferably have the same shape and features. Thus either end 42, 44 may be inserted into the slot 26 of the plate.

Figure 6:
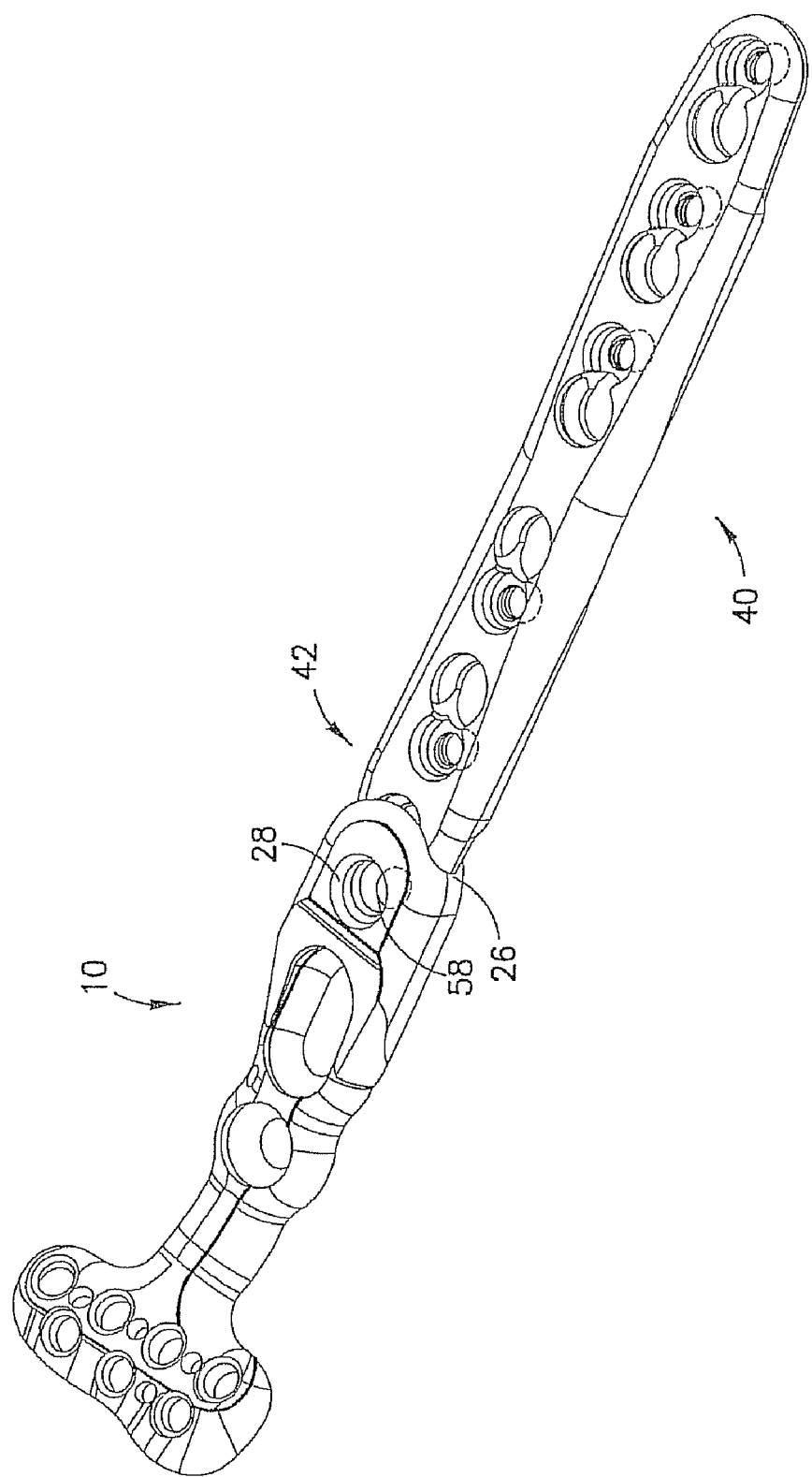
FIG. 6 is a top perspective view of the volar plate with the fragment plate inserted into the slot at the end of the volar plate stem.
Figure 7:
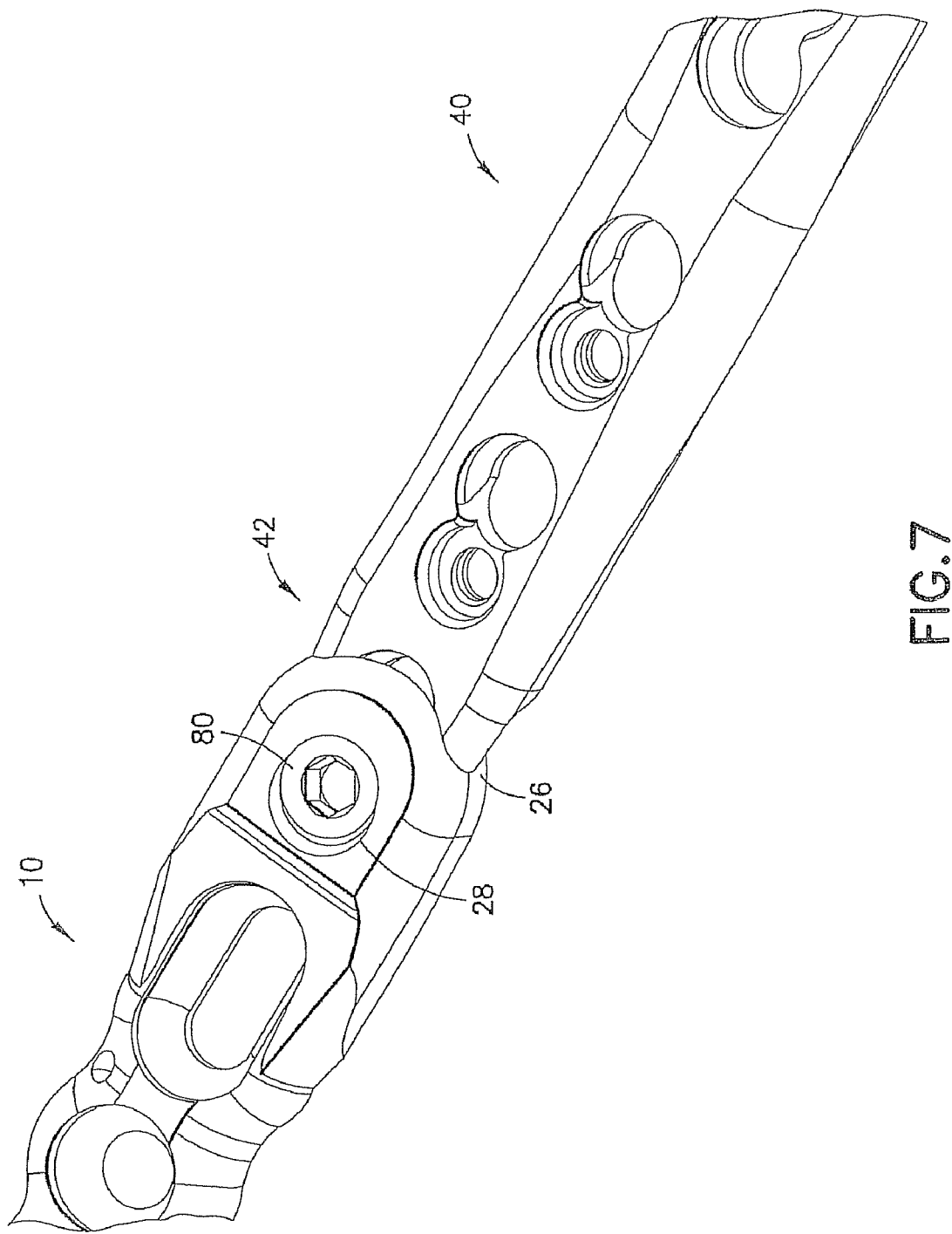
FIG. 7 is an enlarged broken top perspective view showing the mating of the volar plate and the fragment plate with a set screw.
Figure 8:
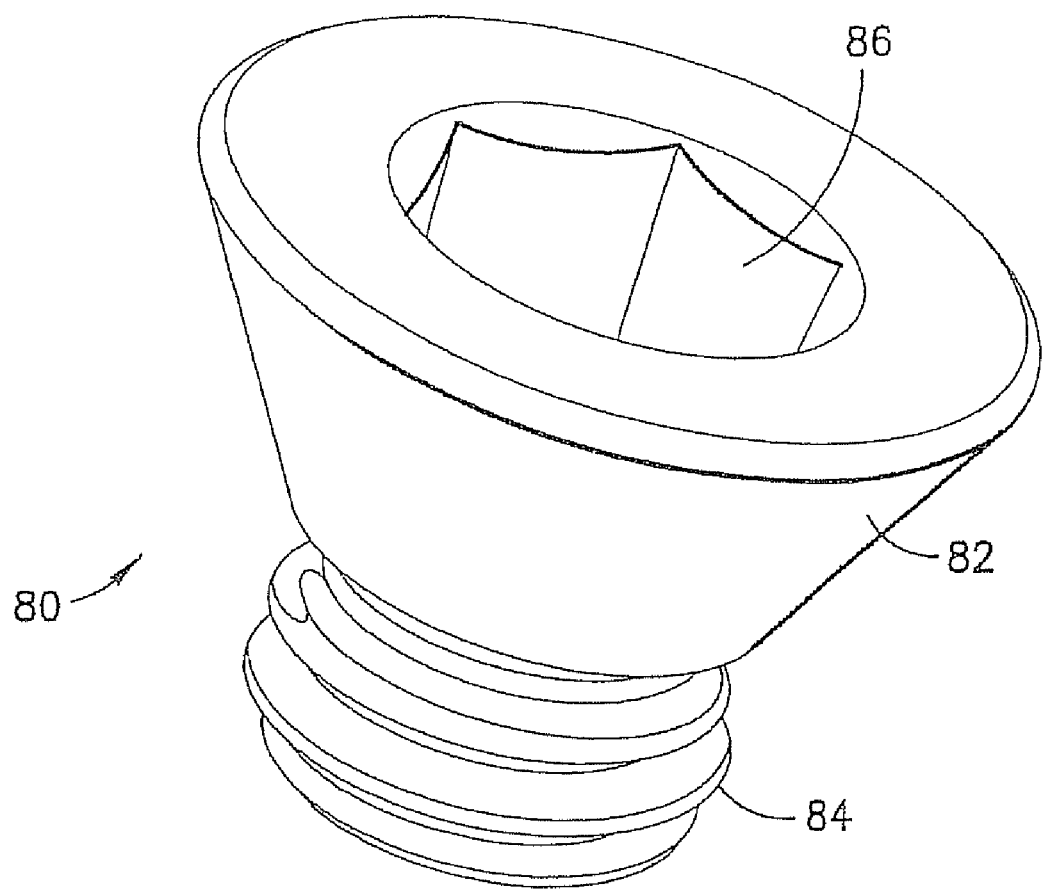
FIG. 8 is an enlarged perspective view of the set screw.

FIG. 6 shows the end 42 of the plate 40 inserted into the slot 26 of the plate 10. The tapered and rounded end 42 of the plate 40 is shaped and dimensioned to fit neatly into the slot 26 of the volar plate 10 with the threaded set screw hole 58 of the plate 40 aligning with the unthreaded set screw hole 28 of the plate 10. When the two plates are arranged as shown in FIG. 6, a set screw 80 is inserted into the hole 28 as shown in FIG. 7. When so inserted, the set screw 80 is threaded into the threaded set screw hole 58 in the plate 40. This secures the two plates together so that they function as a single piece. It is an important aspect of the invention that the distal radius plate and fragment plate be joined without reliance on the bone to join them. Otherwise, the tight interface and coupling between the plates could be compromised based on the quality of the bone, e.g., where such bone is fractured beneath the location of the coupling or where the bone is osteoporotic.

The set screw 80 has a frustoconical head 82 from which depends a threaded stem 84. The head 82 has a hex socket 86 adapted to receive a driver (not shown). The set screw provides a secure lock between the two plates independent of the bone.

By having a threaded set screw hole 58, 68 located near each end of the fragment plate, each such hole can be used to lock the fragment plate to the volar plate, or may alternatively be used to lock an adjacent bone screw in a bone screw hole 46, 56 in place.

In accord with the invention, the end plate 10 at the slot 26 and the fragment plate 40 are substantially similar in thickness, preferably within approximately 30% of each other, and more preferably approximately 26% (end plate=0.145" and fragment plate=0.115"). The relatively close thicknesses are possible, for one reason, in that the end plate does not need to support the compressive forces of bone screws at that location. Rather, as discussed above, the set screws used exert a substantially smaller force on the upper thinner portion of the end plate than would a cortical screw under compressive load.

It is appreciated that the end plate and fragment plate components, separately machined or otherwise formed from each other, will invariably differ, within tolerances, from their specified designs. Such variations from predefined dimensions may cause the components when assembled to have some 'play'. Any play between the components reduces the ability of the assembly to transfer load from one component to the other. Play also results in micromovement of the components that may hamper the healing process. In view of the above, the second and third embodiments are provided.

Turning now to FIGS. 9 through 14, the second embodiment of a modular plate system, including an end plate 110 and a fragment plate 140, is shown. The end plate 110 includes stem portion 114 that is larger in width and thickness at a free end opposite the head portion 112. The underside of the free end 115 is open defining a socket in the form of a cavity 126 into which a post 128 descends. The surface 129 from which the post descends is flat. The cavity 126 tapers in width and defines at an end a portion 130 stepped down in width. The end portion defines opposing flat parallel wall portions 131a, 131b. The stem portion 114 includes a slightly oval set screw hole 132 into the cavity, located between the post 128 and the stepped down portion 130 of the cavity. The centers of the post 128 and set screw hole 132 are intended to be offset by a first distance within a defined tolerance. An oval cortical bone screw hole 134 is also provided in the thinner portion of the stem.

The fragment plate 140 is similar to plate 40, but includes ends 145 stepped down in width and sized to fit within the stepped down portion 130 of the cavity 126. Such ends 145 include short opposing parallel flat sides 147a, 147b. In addition, the upper surface 150 of the fragment plate over the last threaded set screw hole 146 and bone screw hole 158 (i.e., that portion that will be received within the cavity, as described below) is flat to seat stably against flat surface 129 in the cavity. The last set screw hole 146 and bone screw hole 158 are offset from each other by a second distance within a defined tolerance. The second distance is slightly larger than the first defined distance. Also, as an option, several of the screw holes, e.g., 160 (FIG. 9), along the fragment plate are non-locking oblong cortical screw holes.

The set screw 180 includes a head 182 and a shaft 184. Head 182 defined by two frustoconical sections: the upper frustoconical section 182a is angled to seat against the rim 132a of the set screw hole 132, whereas the lower frustoconical section 182b is angle to seat within the upper portion 146a of the set screw hole 146 at the end of the fragment plate.

Figure 13:
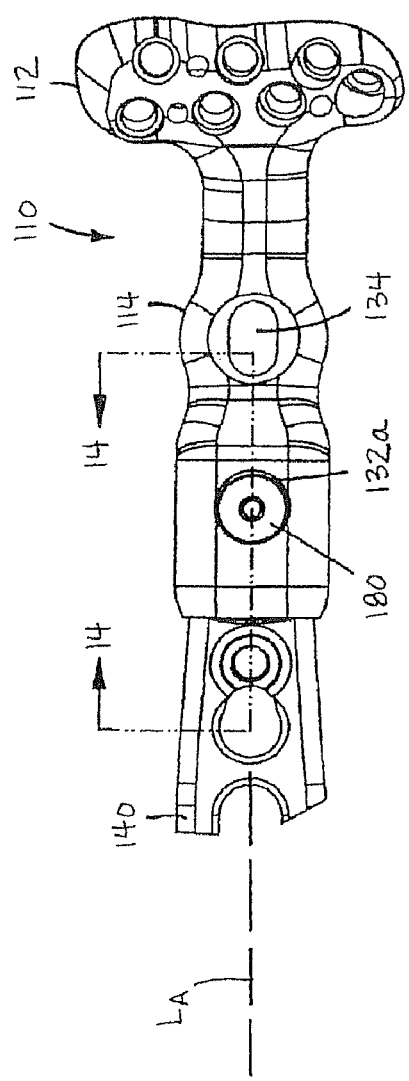
FIG. 13 is a broken top view of the embodiment of FIG. 9.
Figure 14:
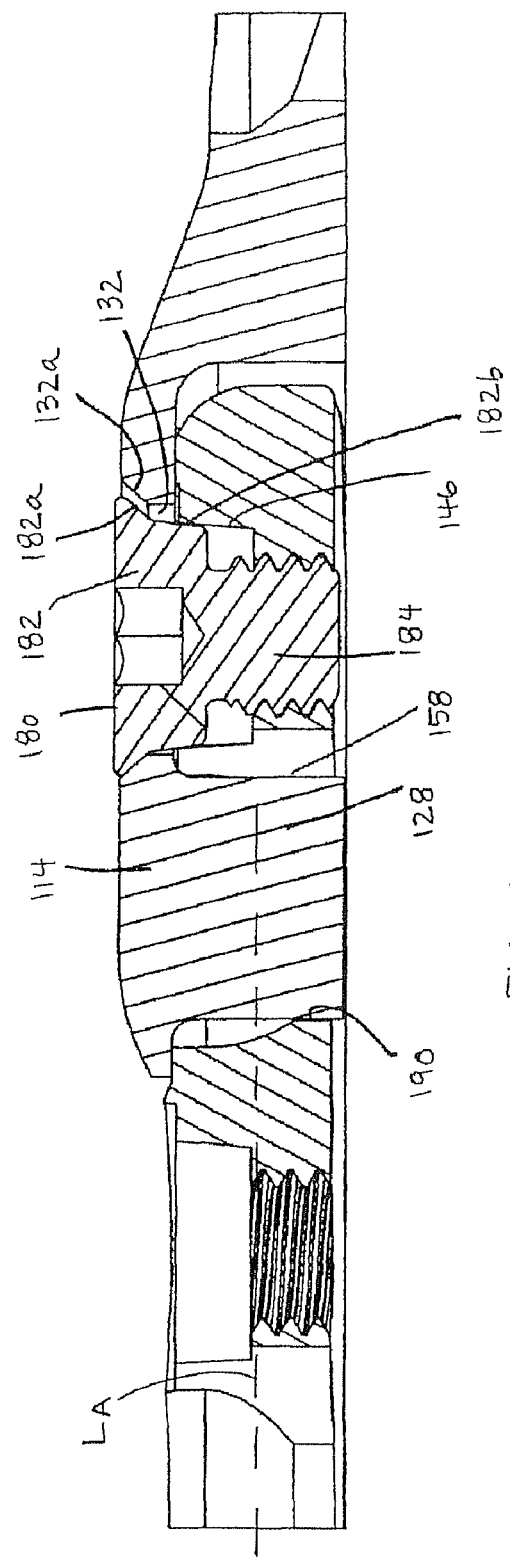
FIG. 14 is a section view across line 14-14 in FIG. 13.

Referring to FIGS. 13 and 14, in assembly, an end 145 of the fragment plate is positioned with the cavity 126 of the end plate 110 and the post 128 is inserted into bone screw hole 158. Given the differences between the first and second defined offset distances, the threads of set screw hole 146 do not perfectly align with the center of non-threaded set screw hole 132. However, the shaft 184 of the set screw 180 is easily maneuvered through set screw hole 132 and into engaged within the threads of the screw hole 146. As the upper section 182a of the head 182 contacts the rim 132a of screw hole 132, the set screw 180 provides a force to push the post 128 of the end plate 110 against the fragment plate (at 190) causing significant interference so as to remove any play. As a result, in axial load, all force is transferred from the end plate to the fragment plate. In addition, when the end plate is subject to torsional force, the flat sides 147a, 147b of the fragment plate being in close contact with flat walls 131a, 131b limits rotation of the components relative to each other. The walls 131a, 131b are of sufficient length to accommodate the range of tolerances to which the components may be manufactured; i.e., so that flat sides 147a, 147b are always adjacent some portion of the flat walls 131a, 131b.

Turning now to FIGS. 15 through 20, the third embodiment of a modular plate system, including an end plate 210 and a fragment plate 240, is shown. The end plate 210 is substantially similar to end plate 110, with the following differences. The enlarged free end includes a widthwise tapered cavity 226 provided with a post 228, and two slightly oblong non-threaded set screw holes 232, 233 entering the cavity 226 one on either side of the post 228. Post 228 and screw hole 232 are offset by a first distance within a defined tolerance. The thinner portion of the end plate includes a preferably oblong non-threaded bone screw hole 234.

The fragment plate 240 is similar to plate 140 with the following differences. The ends 245 are rounded and do not include the stepped end. The last set screw hole 246 and bone screw hole 258 are offset from each other by a second distance within a defined tolerance. Another machine threaded screw hole 260 is provided independent of a cooperative non-threaded bone screw hole. The screw hole 260 is preferably defined by two spaced apart cantilevers 262, 264 set off from the interior of the plate by slots 266, 268 extending generally parallel to the longitudinal axis of the plate. In addition, a recess 270 is provided at the upper portion of the screw hole 260.

Referring to FIGS. 19 and 20, in assembly, an end 245 of the fragment plate is positioned with the cavity 226 of the end plate 210 and the post 228 is inserted into bone screw hole 258. Given the differences between the first and second defined offset distances, the threads of set screw hole 246 do not perfectly align with the center of non-threaded set screw hole 232. However, the shaft 284a of the set screw 280a is easily maneuvered through set screw hole 232 and into engaged within the threads of the screw hole 246. As the upper section 282a of the head 282a contacts the rim 232a of screw hole 232, the set screw 280a provides a force to push the post 228 of the end plate 210 against the fragment plate (at 290) causing significant interference so as to remove any play. As a result, in axial load, all force is transferred from the end plate 210 to the fragment plate 240. The second set screw 280b is inserted into screw hole 233. When set screw 280b is fully seated, the chamfer of at the lower side of head portion 282b' contacts the chamfer about screw hole 233 regardless of the position of the end plate 210 relative to the fragment plate 240. Thus, when the end plate 240 is subject to torsional force, screw 280b limits rotation of the components relative to each other.

In one exemplar embodiment, the end plate 210 at the socket 226 has a thickness of approximately 0.17" and the fragment plate 240 has a thickness of 0.135" at the portion positioned within the socket. As such, in accord with the first embodiment, the thickness of the coupling is less than approximately 30 percent and approximately 26 percent. The second embodiment can be constructed with similar relative dimensions.

In addition, referring to FIG. 15, the end 245a of the fragment plate 240 which is not coupled to the end plate 210 also includes a machine threaded screw 260a, as described above with respect to 260. Such screw hole 260a and the associated framelike structure of the plate thereabout decreases the rigidity of the plate at that location. As such, any cortical screw implanted into bone at the end 245a, and the bone thereabout, will be subject to reduced maximum stress. In addition, the end 245a of the plate can be adjusted in rigidity. By inserting a set screw or other insert into screw hole 260a the fragment plate is made more rigid. Recess 270 allows countersinking of such a set screw. For example, without the set screw the plate may have a flexibility of 0.003 inch, whereas with the set screw inserted, the flexibility is reduced to 0.001 inch. It is appreciated that in some circumstances it is desirable to have a fragment plate that is flexible at its ends, while in other instances, e.g., when the fracture is more comminuted, it is advantageous to have a plate that is less flexible during the healing process. In addition, assuming that a comminuted bone fracture completely heals after a period of time, it may be advantageous to have a plate that after healing allows the bone to function under normal conditions and does not produce high stress concentrations at the cortical screw-bone interface. As such, the set screw or insert can be bioabsorbable, maintaining needed fixation during the healing process, followed by absorption such that the plate has higher stiffness during healing and more flexible thereafter. The resultant plate system would be less likely to result in refracture due to the weakening attributed with drilling holes in the bone and then point loading at those holes.

According to an important aspect of the invention, the plates 10 (10, 210) and 40 (140, 240) are arranged in a kit containing several different size plates 10 and several different size fragment plates 40. According to the presently preferred embodiment, three different size volar plates are provided: standard, wide, and narrow. A plurality of different length fragment plates are also provided. The fragment plates may be straight or curved. For example, the plate may be curved in the plane of the plate to match the radius of curvature of the volar side of the radius bone, e.g., r=23 inches over approximately eighty percent of the length of the plate. The fragment plates can be used alone or in combination with the volar plates. When used together, distal and mid-shaft fractures can be covered with one integral plate (i.e. the two plates coupled to each other as shown in FIG. 7). Thus, the loads are shared by the combined plate rather than the bone between two plates. The load is thereby spread out rather than concentrated on the bone between two plates. The modularity of the different size plates allows for the assembly of a wide variety of combinations using only a few different sizes. For example, three different width volar plates packed together with five different length fragment plates can be used to construct fifteen different size combination plates using only eight different size pieces.

According to an alternate embodiment of the invention, the volar plate is not required to include a socket in the form of a slot or cavity for receiving an end portion of the fragment plate. Rather, a discrete coupler with sockets at two of its sides can be provided between the volar and fragment plates. The coupler operates to "splice" together the metaphyseal volar plate and the diaphyseal fragment plate. The advantage is that the volar plate for use in the system can be a standard component without modification, and can therefore be used alone without the fragment plate. Thus, the surgical tray will need fewer of the more expensive volar plates. In addition, the coupler allows "splicing" of multiple diaphyseal fragment plates together to make one extra long plate.

There have been described and illustrated herein embodiments of a fixation plate, and particularly plates for fixation of distal radius fractures. While particular embodiments of the invention have been described, it is not intended that the invention be limited thereto, as it is intended that the invention be as broad in scope as the art will allow and that the specification be read likewise. Thus, while particular preferred materials, dimensions, and relative angles for particular elements of the system have been disclosed, it will be appreciated that other materials, dimensions, and relative angles may be used as well. Further, while the invention has been described with respect to distal volar radius plates, the invention may include other 'end' plates suitable in size and shape for placement at other metaphyseal locations, e.g., the dorsal side of the distal radius, the humerus, the femur and the tibia. In addition, end plates having shapes other than a 'T' may also be used, such as lateral and medial columns (generally 'L'-shaped), and plates having a flared or forked head, provided such end plates are dimensioned and configured for placement at the metaphysis. In addition, while a particular number of screw holes in the end plate and fragment plate have been described, it will be understood a different numbers of screw holes may be used. Also, fewer or more threaded holes (for pegs or locking screws) may be used. In addition, while a particular preferred angle between the head and stem of the volar plate has been disclosed, other angles can also be used. It will therefore be appreciated by those skilled in the art that yet other modifications could be made to the provided invention without deviating from its scope.

What is claimed is:

1. A fracture fixation plate system for use on a long bone having a metaphysis and a diaphysis, comprising:
   a) at least one end plate having a head portion for the metaphysis defining a plurality of fixation holes for receiving fixation elements that extend into the bone, a bone contacting first surface and an opposite second surface;
   b) at least one fragment plate having a first end and a second end with a plurality of bone screw holes therebetween, wherein
      said at least one end plate defines a socket that receives at least one end of said at least one fragment plate, a non-threaded oblong first hole in said second surface intersecting said socket, and a post formed within said socket and extending from a floor of the socket and away from said second surface and toward the bone on which said first surface is positioned, and said at least one end of said fragment plate has a threaded second hole and a third hole, said at least one end is dimensioned to fit into said socket with said threaded second hole being at least partially aligned with said non-threaded first hole of said end plate and said third hole is dimensioned to receive said post; and c) a set screw dimensioned to enter said non-threaded oblong first hole in said end plate and engage said threaded second hole in said fragment plate, wherein driving said set screw along its axis into said second hole causes longitudinal displacement of said end of said fragment plate relative to said end plate in a direction transverse to the axis of said set screw and results in forcing said post against a periphery of said third hole and rigidly locking the fragment plate into engagement with the end plate.

2. A system according to claim 1, wherein:
said at least one end plate is a plurality of plates having head portions of different sizes,
said at least one fragment plate is a plurality of different length fragment plates,
said end plates and said fragment plates adapted to be mixed and matched and coupled to each other.

3. A system according to claim 1, wherein:
said fixation holes are threaded to receive fixation elements which lock relative to said head portions of said at least one end plate.

4. A system according to claim 1, wherein:
said end plate includes a stem angled relative to said head portion, and said socket and post are integrated into said stem.

5. A system according to claim 1, wherein:
said socket and said at least one end of said fragment plate each have portions which are stepped in width and include flats along the lateral sides thereof.

6. A system according to claim 1, wherein:
said end plate defines a non-threaded fourth hole intersecting the socket, and
said at least one end of said fragment plate has a threaded fifth hole, wherein when said fragment plate is mated with said end plate said threaded fourth hole is aligned with said non-threaded fifth hole.

7. A system according to claim 6, wherein:
said non-threaded fourth hole is oblong.

8. A system according to claim 1, wherein:
said fragment plate includes a threaded fourth hole defined by two spaced apart cantilevers.

9. The system according to claim 8, further comprising:
c) a second screw dimensioned to enter said threaded fourth hole, wherein when said second screw is inserted into said threaded fourth hole, the rigidity of said fragment plate surrounding said threaded fourth hole is increased.

10. A system according to claim 1, wherein:
said fragment plate includes a longitudinal midpoint, and for each bone screw hole, a threaded set screw hole is provided on a side of the bone screw hole closer to an end of the fragment plate than the midpoint.

11. A system according to claim 1, wherein:
said head portion is sized and shaped for the distal volar radius bone.

* * * * *